US00PP31886P2

(12) United States Plant Patent
Dibley

(10) Patent No.: US PP31,886 P2
(45) Date of Patent: Jun. 16, 2020

(54) ***BEGONIA* PLANT NAMED 'BDICM02-0'**

(50) Latin Name: *Begonia rex-cultorum*
Varietal Denomination: BDICM02-0

(71) Applicant: Lynne Dibley, Ruthin (GB)

(72) Inventor: Lynne Dibley, Ruthin (GB)

( * ) Notice: Subject to any disclaimer, the term of this patent is extended or adjusted under 35 U.S.C. 154(b) by 0 days.

(21) Appl. No.: 16/350,692

(22) Filed: Dec. 18, 2018

(51) Int. Cl.
*A01H 5/12* (2018.01)
*A01H 6/18* (2018.01)

(52) U.S. Cl.
USPC ..... Plt./343

(58) Field of Classification Search
USPC ..... Plt./343
CPC ... A01H 5/12; A01H 5/02; A01H 5/00; A01H 5/0238; A01H 6/18; A01H 6/185
See application file for complete search history.

*Primary Examiner* — June Hwu
(74) *Attorney, Agent, or Firm* — Cassandra Bright

(57) ABSTRACT

A new and distinct *Begonia rex-cultorum* cultivar named 'BDICM02-0' is disclosed, characterized by a large cordate and overlapping foliage of silvery green dominated by a thick main veins of dark greyed-purple and red mid-leaf section. Plants are upright and grow rapidly. The new variety is a *Begonia*, and is normally used as an ornamental garden or container plant.

1 Drawing Sheet

Latin name of the genus and species: *Begonia rex-cultorum.*

Variety denomination: 'BDICM02-0'.

BACKGROUND OF THE INVENTION

The new cultivar is the product of a planned breeding program. The new variety originated as the result of an open pollination performed during August of 2014 of an unnamed, unpatented proprietary *Begonia rex-cultorum*, and several unnamed, unpatented proprietary *Begonia rex-cultorum* pollen parents. The selection of the new variety was made during 2015 by the inventor at a research greenhouse located in Wales, UK.

Asexual reproduction of the new cultivar 'BDICM02-0' was first performed at a research greenhouse located in Wales, UK by terminal vegetative cuttings during 2015. 'BDICM02-0' has since produced several generations by vegetative cuttings and has shown that the unique features of this cultivar are stable and reproduced true to type.

SUMMARY OF THE INVENTION

The cultivar 'BDICM02-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BDICM02-0.' These characteristics in combination distinguish 'BDICM02-0' as a new and distinct *Begonia tuberhybrida* cultivar:

1. Upright plant habit.
2. Large cordate leaf with slightly overlapping base.
3. Rapid growth.
4. Unique leaf color with a an over silvery grey-green color dominated by thick main veins of dark greyed-purple, lighter Greyed-Purple(187C) mid-leaf section and well-defined dark margins.
5. Greyed-Purple petioles.

PARENT COMPARISON

Plants of the new cultivar 'BDICM02-0' are similar to plants of the seed parent variety in most horticultural characteristics. However, plants of the new cultivar 'BDICM02-0' differ in the following:

1. Leaves of the new variety are larger than leaves of the seed parent.
2. Leaves of the new variety have a cordate and slightly overlapping base, foliage base of the seed parent are obtuse and non-overlapping.
3. Petioles of the new variety are greyed-purple, petioles of the seed parent are green.

COMMERCIAL COMPARISON

Plants of the new cultivar 'BDICM02-0' are similar to plants of the commercial variety, *Begonia maculata* 'Wightii', unpatented, in most horticultural characteristics. However, plants of the new cultivar 'BDICM02-0' differ in the following:

1. Foliage of the new variety is larger.
2. Foliage of the new variety has a lighter Greyed-Purple (187C) mid-leaf section not found in this comparator.
3. Plants of the new variety are shorter than plants of this comparator.

Plants of the new cultivar 'BDICM02-0' are similar to plants of the commercial variety, *Begonia* 'Connee Boswell', unpatented, in most horticultural characteristics. However, plants of the new cultivar 'BDICM02-0' differ in the following:

1. Foliage of the new variety is larger.
2. Foliage of the new variety has a lighter Greyed-Purple (187C) mid-leaf section not found in this comparator.

3. Plants of the new variety are shorter than plants of this comparator.
4. Leaves of the new variety, have a cordate and slightly overlapping base, leaf bases of this comparator are hastate and non-overlapping.
5. Plants of the new variety grow faster than plants of this comparator.

BRIEF DESCRIPTION OF THE PHOTOGRAPH

The present invention of a new and distinct variety of *Begonia* is shown in the accompanying photographs, the colors being as nearly true as possible with color photographs of this type. Age of the plant is approximately 16 weeks, shown in a 6-inch pot.

DETAILED BOTANICAL DESCRIPTION

In the following description, color references are made to The Royal Horticultural Society Colour Chart 2007 except where general terms of ordinary dictionary significance are used. The following observations and measurements describe 'BDICM02-0' plants grown in a commercial controlled greenhouse in Santa Paula, Calif. Measurements and numerical values represent averages of typical plant types.

Botanical classification: *Begonia rex-cultorum* 'BDICM02-0'.

Age of plant described: Approximately 12 weeks.

Container of plant described: 4-inch pot.

PROPAGATION

Type of propagation typically used: Vegetative tip cuttings.

Time to develop roots: About 10 days at approximately 21° C.

Time to develop a rooted liner: About 21 days at approximately 21° C.

Root description: Fibrous, fine, well branched. White and tan, not accurately measured with the RHS chart.

PLANT

Growth habit: Upright growing, fleshy annual.

Plant shape: Upright, "V" shape.

Pot size of plant described: 4-inch.

Height: Approximately 28 cm.

Plant spread: Approximately 48 cm.

Growth rate: Rapid.

Branching characteristics: Basally emerging foliage, no actual branches, only petioles.

FOLIAGE

*Type.*—Single, basally emerging foliage and long petioles.

*Orientation.*—Mainly upwardly facing foliage. Lower, oldest foliage outwardly facing.

*Strength.*—Very strong, hard foliage, resists breakage.

*Texture, top surface.*—Rugose.

*Texture lower surface.*—Main surface non-pubescent, veins sparsely hirsute. Largest veins more densely hirsute. Hairs approximately 0.2 to 3 m long, colored near RHS Greyed-Purple 186D.

*Appearance.*—Metallic, matte and slightly leathery appearance to upper surface. Lower surface matte.

*Quantity.*—Approximately 18 to 24.

*Shape of blade.*—Overall cordate, with base curling back slightly overlapping main leaf.

*Apex.*—Acute.

*Base.*—Cordate, slightly overlapping top of leaf surface.

*Margin.*—Incised and serrate. Sinuses acute, approximately 50 to 15 mm deep. Infrequently occurring, short, sharp hairs, approximately 1 to 3 mm length and colored near RHS Greyed-Purple N187C.

*Aspect.*—Irregularly undulating.

Mature leaves:

*Average length.*—Average range 20 to 28 cm.

*Average width.*—Average range 15 to 19 cm.

*Color.*—Mature foliage upper side: Center blotch, approximately 20 to 30% of leaf blade RHS Greyed-Purple 187C. Rugose ridges through blotch colored near Greyed-Purple N186A. Veins in blotch colored near Greyed-Purple 186D. Beyond the center blotch, main leaf blade color changes to Greyed-Green 191C with rugose ridges colored Green 137A, with blotches along ridges colored Green 137A. Well defined margin colored near Greyed-Purple N186B, edge of margin tinged Greyed-Purple 186C. Mature foliage under side: Near RHS Greyed-Green 191B and 191C, colors present individually. Center blotch near petiole attachment heavily flushed Greyed-Purple 187C. Flushed 187C near veins. Veins 187C. Margin near Greyed-Purple 187A.

*Venation.*—Type: Palmate. Venation color upper side: From Petiole attachment to approximately ⅔ length of blade colored near RHS Greyed-Purple 186D. Outer ⅓ near Green 137A. Venation color under side: Near RHS Greyed-Purple 187C.

Immature leaves:

*Average length.*—Approximately 11 cm.

*Average width.*—Approximately 9 cm.

*Color.*—Immature foliage upper side: Center blotch, approximately 10 to 20% of leaf blade RHS Greyed-Purple 187C. Rugose ridges through blotch colored near Greyed-Purple N186A. Veins in blotch colored near Greyed-Purple 186D. Beyond the center blotch, main leaf blade color changes to Greyed-Green 191C with rugose ridges colored Green 137A, with blotches along ridges colored Green 137A. Well defined margin colored near Greyed-Purple N186B, edge of margin tinged Greyed-Purple 186C. Immature foliage under side: Near RHS Greyed-Green 191B and 191C, colors present individually. Small center blotch near petiole attachment heavily flushed Greyed-Purple 187C. Flushed 187C near veins. Veins 187C. Margin near Greyed-Purple 187A.

*Venation.*—Type: Palmate. Venation color upper side: From Petiole attachment to approximately ⅔ length of blade colored near RHS Greyed-Purple N187A. Outer ⅓ near Greyed-Green 191A. Venation color under side: Near RHS Greyed-Purple 187A.

*Petiole.*—Length: Average range 12 to 16 cm. Diameter: Approximately 6 to 7 mm. Color: Background color near RHS Yellow-Green 152B, completely flushed Greyed-Purple 187D. Texture: Hirsute. Sparsely to moderately dense Hairs approximately 3 mm long, colored near RHS White 155C.

*Stipule description.*—Length: Approximately 1.2 cm. Diameter: Approximately 1.2 cm. Shape: Deltate. Apex: Acute. Base: Truncate. Color: Immature near RHS Greyed-Purple 187C, upper and lower surfaces. Dries to Grey-Brown 199B, upper and lower surfaces, before leaf matures. Texture: Upper Surface: Very sparsely pilose. Lower Surface: Glabrous.

FLOWER

Not observed to date.

REPRODUCTIVE ORGANS

Not observed to date.

OTHER CHARACTERISTICS

Seeds and fruits: Not observed to date.

Disease/pest resistance: Neither resistance nor susceptibility to diseases or pests of *Begonia* has been observed in this variety.

Temperature tolerance: The new variety tolerates temperatures from approximately 5° to 35° C.

What is claimed is:

1. A new and distinct cultivar of *Begonia rex-cultorum* plant named 'BDICM02-0' as herein illustrated and described.

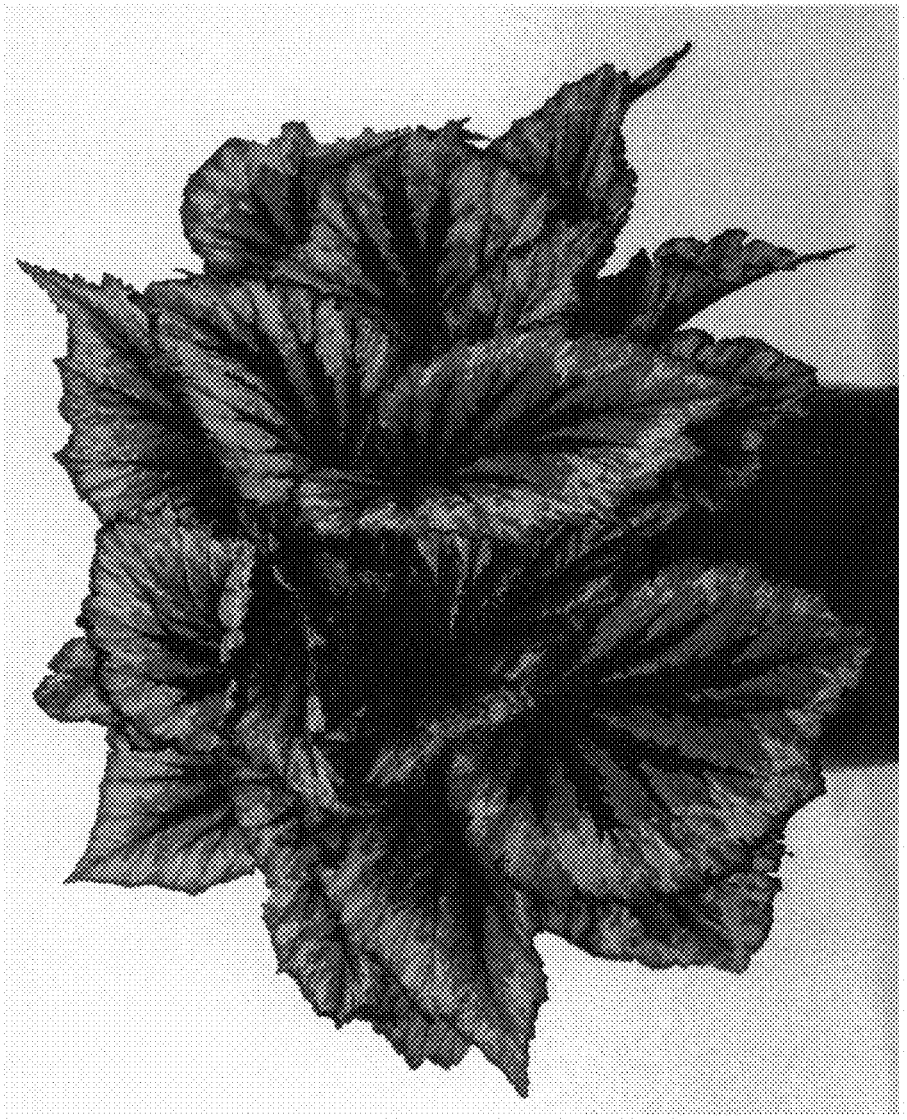

* * * * *